United States Patent
Geng et al.

(10) Patent No.: US 12,350,636 B2
(45) Date of Patent: Jul. 8, 2025

(54) GENE SEQUENCING CHIP AND GENE SEQUENCING METHOD

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Yue Geng, Beijing (CN); Fengchun Pang, Beijing (CN); Peizhi Cai, Beijing (CN); Le Gu, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 722 days.

(21) Appl. No.: 17/683,059

(22) Filed: Feb. 28, 2022

(65) Prior Publication Data

US 2022/0184577 A1    Jun. 16, 2022

Related U.S. Application Data

(63) Continuation of application No. 16/071,932, filed as application No. PCT/CN2018/070032 on Jan. 2, 2018, now Pat. No. 11,291,970.

(30) Foreign Application Priority Data

May 12, 2017    (CN) .......................... 201710334710.1

(51) Int. Cl.
  *B01J 19/00* (2006.01)
  *C12Q 1/6874* (2018.01)

(52) U.S. Cl.
  CPC ........ *B01J 19/0046* (2013.01); *C12Q 1/6874* (2013.01); *B01J 2219/00479* (2013.01); *B01J 2219/00529* (2013.01); *B01J 2219/00608* (2013.01); *B01J 2219/00722* (2013.01)

(58) Field of Classification Search
  None
  See application file for complete search history.

(56) References Cited

U.S. PATENT DOCUMENTS

| | | |
|---|---|---|
| 2009/0280475 A1 | 11/2009 | Pollack |
| 2009/0280476 A1 | 11/2009 | Srinivasan et al. |
| 2013/0096013 A1 | 4/2013 | Esfandyarpour et al. |
| 2013/0116128 A1 | 5/2013 | Shen |
| 2014/0034497 A1 | 2/2014 | Davis et al. |
| 2014/0262783 A1 | 9/2014 | Chang |
| 2015/0336098 A1 | 11/2015 | Pollack |
| 2016/0114320 A1 | 4/2016 | Pollack |

FOREIGN PATENT DOCUMENTS

| | | |
|---|---|---|
| CN | 104105797 A | 10/2014 |
| CN | 104350162 A | 2/2015 |
| CN | 107118955 A | 9/2017 |

OTHER PUBLICATIONS

Office action from U.S. Appl. No. 16/071,932 dated May 3, 2021.
Office action from Chinese Application No. 201710334710.1 dated Sep. 2, 2019.
Office action from Chinese Application No. 201710334710.0 dated Feb. 11, 2019.
Search Report from European Application No. 18739446.5 dated Dec. 9, 2020.
International Search Report and Written Opinion from PCT/CN2018/070032 dated Apr. 8, 2018.

*Primary Examiner* — Christopher M Gross
(74) *Attorney, Agent, or Firm* — Calfee, Halter & Griswold LLP

(57) ABSTRACT

A gene sequencing chip is provided, which includes: an upper substrate including a plurality of liquid inlets for inletting liquid drops; a lower substrate opposite to the upper substrate and spaced therefrom by a gap, the gap being provided for allowing the liquid drops to move therein, the lower substrate including a liquid drop operation region, the liquid drop operation region including a manipulation electrode array. The manipulation electrode array includes multiple first manipulation electrode array for preparing a gene library, multiple second manipulation electrode array for sequencing the gene library which is prepared, each first sub-array being adjacent to one of the multiple second manipulation electrode array. Based on the gene sequencing chip provided in this disclosure, operations to tiny liquid drops such as movement, fusion and splitting can be accurately manipulated by using digital microfluidic techniques, and all steps of the gene sequencing from library preparation to gene sequencing can be completed on one chip.

12 Claims, 3 Drawing Sheets

GENE SEQUENCING CHIP AND GENE SEQUENCING METHOD

CROSS REFERENCE TO RELATED APPLICATIONS

The present application is a continuation application based on a U.S. patent application Ser. No. 16/071,932, which claims the priority of Chinese patent application No. 201710334710.1 filed on May 12, 2017, the entire disclosures of which are incorporated herein by reference.

TECHNICAL FIELD

This disclosure relates to the field of gene sequencing techniques, and in particular to a gene sequencing chip and a gene sequencing method.

BACKGROUND

For existing techniques of gene sequencing chip, library preparation and gene sequencing are carried out on different chips respectively. Firstly, a gene library is prepared by manual operation or on a digital chip, and then the prepared library is injected into a sequencing chip to complete sequencing. Such traditional techniques are very mature, for example, Illumina Company uses a digital micro fluidic chip for library preparation and then uses a further sequencing chip to perform gene sequencing. Such a traditional sequencing method requires preparing a gene library separately, and then manually loading the prepared library to a sequencing chip, wherein many manual operations are involved, which is unfavorable to the reduction of a sequencing period. Moreover, since it requires manual loading, only a large library dose can satisfy liquids loss occurring during manual transfer, which increases the consumption of reagents, raises the reagent cost and the time cost and goes against improvement of automation degree and reduction in cost. Besides, traditional chips for sequencing are usually driven based on an electroosmotic flow or a pressure, where large-dimensioned channels and a great many of reagents are required and liquid drops cannot be manipulated accurately, which also raises the cost of sequencing-related reagents. During the traditional gene sequencing, library preparation and gene sequencing are performed by using different techniques and principles, so the entire procedure cannot be carried out on one same chip. Although the fabrication of a corresponding chip is very simple as library preparation and gene sequencing are performed separately, the cost cannot be lowered due to inaccurate metering and use of the reagents.

SUMMARY

Embodiments of this disclosure provide a gene sequencing chip, comprising: an upper substrate including a plurality of liquid inlets for inletting liquid drops, a lower substrate opposite to the upper substrate and spaced therefrom by a gap for depositing the liquid drops, the liquid drops comprising raw material liquid drops, gene library preparation reagent liquid drops, gene amplification reagent liquid drops and gene sequencing reagent liquid drops. The lower substrate comprises a liquid drop operation region, the liquid drop operation region comprises: at least one first manipulation electrode array, each first manipulation electrode array comprising a plurality of first manipulation electrodes arranged in a row in a first direction and spaced apart from each other, the first manipulation electrode array being configured to move the raw material liquid drops and the gene library preparation reagent liquid drops; at least one second manipulation electrode array, each second manipulation electrode array comprising a plurality of second manipulation electrodes arranged in a row in the first direction and spaced apart from each other, the second manipulation electrode array being configured to move the gene amplification reagent liquid drops and the gene sequencing reagent liquid drops; and a rectangular ring-shaped array comprising a plurality of third manipulation electrodes spaced apart from each other and forming a rectangular shape, the rectangular ring-shaped array being configured to mix the raw material liquid drops and the gene library preparation reagent liquid drops. The second manipulation electrode array and the first manipulation electrode array are adjacent to each other in a second direction perpendicular to the first direction. The lower substrate further comprises an electrode control region for controlling an energizing sequence for the plurality of first manipulation electrodes, the plurality of second manipulation electrodes and the plurality of third manipulation electrodes to achieve movement of the liquid drops.

In some embodiments, the liquid drop operation region comprises a sample region, a first sample injection region, a second sample injection region and a third sample injection region, wherein the upper substrate further comprises: an inlet port via which the raw material liquid drops are provided to the sample region, the sample region comprising a plurality of sample region manipulation electrodes adjoining the first manipulation electrode array; a first inlet via which the gene library preparation reagent liquid drops are provided to the first sample injection region, the first sample injection region comprising a plurality of first sample injection region manipulation electrodes adjoining the first manipulation electrode array; a second inlet via which the gene amplification reagent liquid drops are provided to the second sample injection region, the second sample injection region comprising a plurality of second sample injection region manipulation electrodes adjoining the second manipulation electrode array; a third inlet via which the gene sequencing reagent liquid drops are provided to the third sample injection region, the third sample injection region comprising a plurality of third sample injection region manipulation electrodes adjoining the second manipulation electrode array. The inlet port, the first inlet, the second inlet and the third inlet all penetrate the upper substrate.

In some embodiments, the upper substrate comprises an outlet port for discharging a waste liquid, and the outlet port penetrates the upper substrate.

In some embodiments, some first manipulation electrodes of the plurality of first manipulation electrodes of the first manipulation electrode array act as some third manipulation electrodes of the plurality of third manipulation electrodes of the rectangular ring-shaped array, so that the first manipulation electrode array comprises a side of the rectangular shape.

In some embodiments, an area of an orthographic projection of the first sample injection region on the upper substrate is greater than an area of an orthographic projection of the third sample injection region on the upper substrate.

In some embodiments, the electrode control region comprises a metal contact point array, the metal contact point array comprises a plurality of metal contact points corresponding to the plurality of first manipulation electrodes, the plurality of second manipulation electrodes and a plurality of third manipulation electrodes.

In some embodiments, the lower substrate further comprises a first glass substrate for carrying the liquid drop operation region and the electrode control region.

In some embodiments, the lower substrate further comprises: a first dielectric layer overlaying the liquid drop operation region, and a first hydrophobic layer arranged on a surface of the first dielectric layer facing away from the first manipulation electrode array and the second manipulation electrode array.

In some embodiments, the upper substrate comprises: a second glass substrate, an ITO reference electrode arranged on a surface of the second glass substrate facing the lower substrate, a second dielectric layer arranged on a surface of the ITO reference electrode facing the lower substrate, and a second hydrophobic layer arranged on a surface of the upper dielectric layer facing the lower substrate.

In some embodiments, the first hydrophobic layer comprises PTFE.

In some embodiments, an area of an orthographic projection of each first manipulation electrode of the first manipulation electrode array on the first glass substrate is greater than an orthographic projection of each second manipulation electrode of the second manipulation electrode array or each third manipulation electrode of the rectangular ring-shaped array on the first glass substrate.

In some embodiments, respective one second manipulation electrode array of the at least one second manipulation electrode array is arranged between every two adjacent first manipulation electrode arrays, respectively.

DETAILED DESCRIPTION OF EMBODIMENTS

Embodiments of the disclosure will be further explained in detail with reference to the drawings and examples. It can be understood that the specific embodiments depicted herein are only used for explaining this disclosure, instead of limiting the invention. Besides, it should be further noted that in order to facilitate depiction, the drawings only show structures of the gene sequencing chip related to the embodiments of this disclosure, instead of all.

Figure 1:
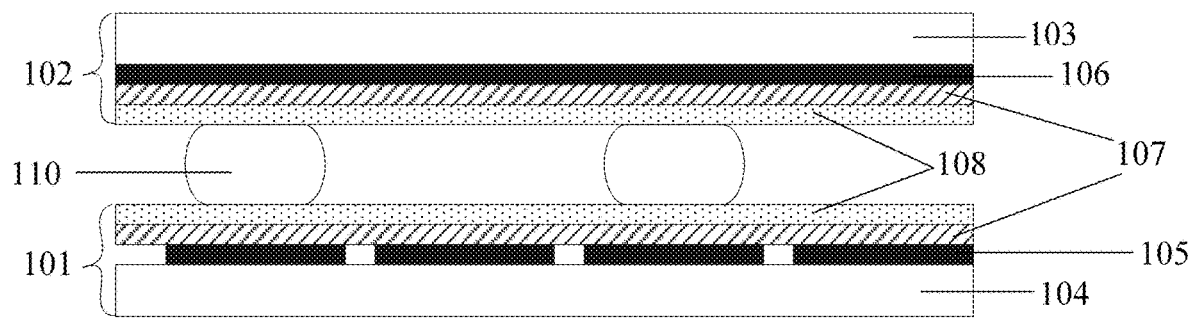
FIG. 1 is a schematic partial sectional view of a gene sequencing chip according to an embodiment of this disclosure.
Figure 2:
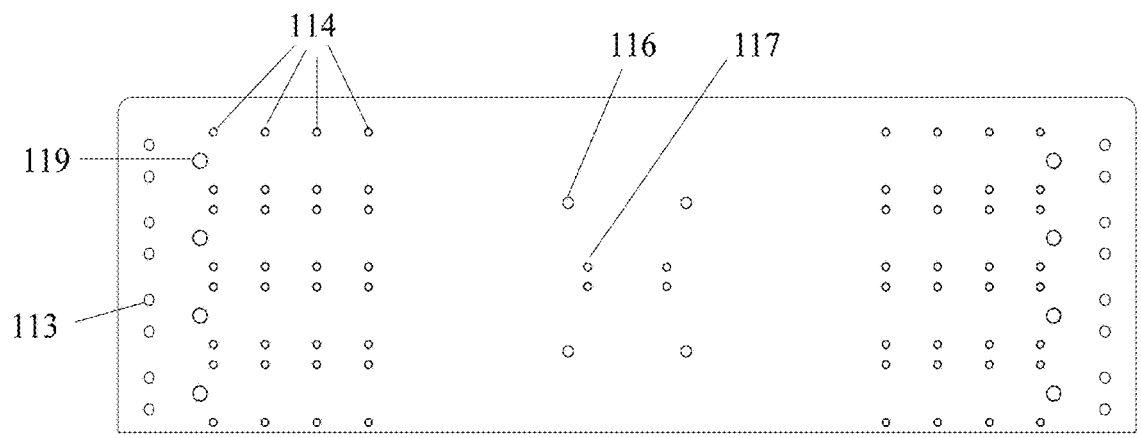
FIG. 2 is a top view of the upper substrate of the gene sequencing chip according to the embodiment of FIG. 1.

The embodiments of this disclosure provide a gene sequencing chip. FIG. 1 schematically shows a partial section view of the gene sequencing chip according to an embodiment of this disclosure. FIG. 2 is a top view of an upper substrate of the gene sequencing chip according to an embodiment of this disclosure.

As shown in FIG. 1, the gene sequencing chip provided in the embodiment of this disclosure comprises an upper substrate 102 and a lower substrate 101, the upper substrate 102 and the lower substrate 101 being spaced from each other by a certain gap, the gap being provided for accommodating liquid drops 110 for test (the liquid drops for test herein comprise raw material liquid drops, gene library preparation reagent liquid drops, gene sequencing reagent liquid drops and so on, which will be mentioned below). As shown in FIG. 2, the upper substrate 102 comprises a plurality of through holes, which form inlets and outlets for various reagents and allows entrance of the liquid drops for test. Referring to FIG. 2, the upper substrate 102 comprises: an inlet port 113 for adding raw material liquid drops, the raw material liquid drops being a basic raw material for preparing a gene library; a first inlet 113 for adding gene library preparation reagent liquid drops, for example, the four first inlets 114 in FIG. 2 are used for adding DNA helicases, reagent for breaking DNA, DNA adapters or the like respectively; a second inlet 116 and a third inlet 117, the second inlet 116 being used for adding reagents related to gene amplification, and the third inlet 117 being used for adding gene sequencing reagent liquid drops, e.g., four fluorescent labeled bases.

The upper substrate 102 further comprises an upper glass substrate 103, an ITO (indium tin oxide) reference electrode 106 arranged on a surface of the upper glass substrate 103 closer to the lower substrate 101, an upper dielectric layer 107 arranged on a surface of the ITO reference electrode 106 closer to the lower substrate 101, and an upper hydrophobic layer 108 arranged on a surface of the upper dielectric layer 107 closer to the lower substrate 101. A material of the upper dielectric layer 107 comprises various polymer materials or silicon oxides, silicon nitrides or the like, and a material of the upper hydrophobic layer 108 comprises PTFE (Polytetrafluoroethylene).

Figure 3:
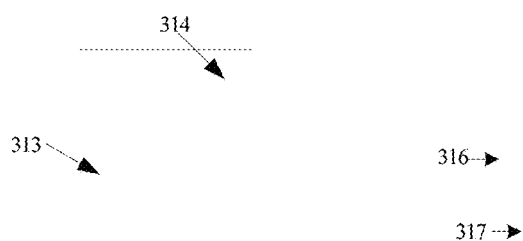
FIG. 3 is a top view of the lower substrate of the gene sequencing chip according to the embodiment of FIG. 1.
Figure 4:
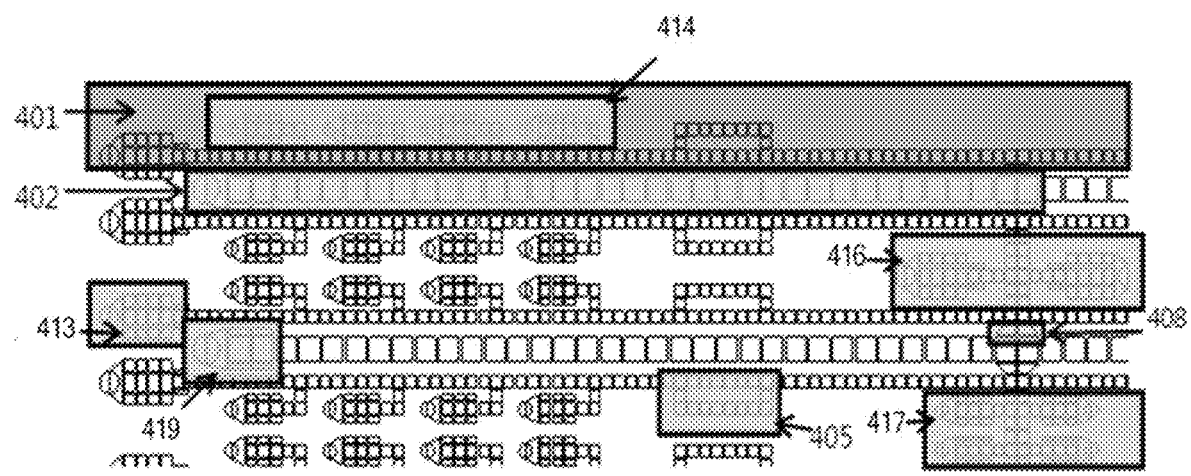
FIG. 4 is a schematic view showing specific details of the lower substrate of the gene sequencing chip according to an embodiment of this disclosure.

The lower substrate 101 comprises a lower glass substrate 104 and a manipulation electrode array 105, the manipulation electrode array 105 being arranged on a surface of the lower glass substrate 104 facing the upper substrate 102. The manipulation electrode array 105 comprises a plurality of manipulation electrodes, each manipulation electrode may have a size of 0.5-5 mm. The manipulation electrodes may have an interval of 0.1-1 mm therebetween, and a material of the manipulation electrodes may include ITO, copper or chromium. That is to say, the manipulation electrodes are spaced apart from each other. The lower substrate 101 further comprises a lower dielectric layer 107 overlaying the manipulation electrode array 105, and a lower hydrophobic layer 108 arranged on a surface of the lower dielectric layer 107 closer to the upper substrate 102. The gene sequencing chip further comprises an electrode control region for controlling the manipulation electrodes in the manipulation electrode array 105, the electrode control region may be arranged in a same layer as the manipulation electrode array. FIG. 3 is a schematic top view of the lower substrate of the gene sequencing chip according to an embodiment of this disclosure. FIG. 4 is a schematic view showing details of the lower substrate of the gene sequencing chip according to an embodiment of this disclosure.

As shown in FIG. 3, the lower substrate 101 comprises: a liquid drop operation region 301; a plurality of manipulation electrodes 303 located in the liquid drop operation region 301 and forming an array; an electrode control region 302 outside the liquid drop operation region 301, the electrode control region controlling an energizing sequence for the plurality of manipulation electrodes 303 to achieve movement of the liquid drops for test above the plurality of manipulation electrodes 303.

As shown in FIG. 4, in the liquid drop operation region 301, the plurality of manipulation electrodes 303 in an array comprise at least one first manipulation electrode array 401 and at least one second manipulation electrode array 402, the first manipulation electrode array 401 being used for preparing a gene library and the second manipulation electrode array 402 being used for sequencing the gene library prepared by the first manipulation electrode array, the first manipulation electrode array 401 being adjacent to the second manipulation electrode array 402.

The first manipulation electrode array 401 in the liquid drop operation region 301 further comprise a rectangular ring-shaped array 405 for mixing the raw material liquid drops and the gene library preparation reagent liquid drops added to the first manipulation electrode array 401.

In summary, as shown in FIGS. 3 and 4, the liquid drop operation region 301 comprises: at least one first manipulation electrode array 401, each first manipulation electrode array 401 comprising a plurality of first manipulation electrodes arranged in a row in a first direction and spaced apart from each other, the first manipulation electrode array 401 being configured to move the raw material liquid drops and the gene library preparation reagent liquid drops; at least one second manipulation electrode array 402, each second manipulation electrode array 402 comprising a plurality of second manipulation electrodes arranged in a row in the first direction and spaced apart from each other, the second manipulation electrode array 402 being configured to move the gene amplification reagent liquid drops and the gene sequencing reagent liquid drops; and a rectangular ring-shaped array 405 comprising a plurality of third manipulation electrodes spaced apart from each other and forming a rectangular shape, the rectangular ring-shaped array being configured to mix the raw material liquid drops and the gene library preparation reagent liquid drops. The second manipulation electrode array 402 and the first manipulation electrode array 401 are adjacent to each other in a second direction perpendicular to the first direction. The lower substrate further comprises an electrode control region 302 for controlling an energizing sequence for the plurality of first manipulation electrodes, the plurality of second manipulation electrodes and the plurality of third manipulation electrodes to achieve movement of the liquid drops.

Additionally, the liquid drop operation region 301 comprises a sample region 313, a first sample injection region 314, a second sample injection region 316 and a third sample injection region 317. The upper substrate comprises: the inlet port 413 via which the raw material liquid drops are provided to the sample region, the sample region comprising a plurality of sample region manipulation electrodes adjoining the first manipulation electrode array; the first inlet via 414 which the gene library preparation reagent liquid drops are provided to the first sample injection region, the first sample injection region comprising a plurality of first sample injection region manipulation electrodes adjoining the first manipulation electrode array 401; the second inlet 416 via which the gene amplification reagent liquid drops are provided to the second sample injection region, the second sample injection region comprising a plurality of second sample injection region manipulation electrodes adjoining the second manipulation electrode array 402; the third inlet 417 via which the gene sequencing reagent liquid drops are provided to the third sample injection region, the third sample injection region comprising a plurality of third sample injection region manipulation electrodes adjoining the second manipulation electrode array 402. The term "adjoining" mentioned herein means being not connected together but spaced apart by a small distance such as the interval of 0.1-1 mm previously mentioned.

In some embodiments, as shown in FIGS. 3 and 4, some first manipulation electrodes of the plurality of first manipulation electrodes of the first manipulation electrode array 401 act as some third manipulation electrodes of the plurality of third manipulation electrodes of the rectangular ring-shaped array 405, so that the first manipulation electrode array comprises a side of the rectangular shape. Further, an area of an orthographic projection of the first sample injection region on the upper substrate is greater than an area of an orthographic projection of the third sample injection region on the upper substrate.

Continuing to refer to FIGS. 3 and 4, an area of an orthographic projection of each first manipulation electrode of the first manipulation electrode array 401 on the first glass substrate is greater than an orthographic projection of each second manipulation electrode of the second manipulation electrode array 402 or each third manipulation electrode of the rectangular ring-shaped array on the first glass substrate. Moreover, as shown in FIG. 3, respective one second manipulation electrode array 402 of the at least one second manipulation electrode array is arranged between every two adjacent first manipulation electrode arrays 401, respectively.

The procedure of gene library preparation and sequencing will be specifically described with reference to FIG. 4. In FIG. 4, the area indicated by 413 corresponds to the inlet port 113 in the upper substrate of FIG. 2. The inlet port, the first inlet for adding reagents for the preparation of the gene library, the second inlet and the third inlet for adding reagents for sequencing the gene library are all formed in the upper substrate by through hole processing. In fact, the lower substrate is not provided with an inlet port, a first inlet, a second inlet, a third inlet or an outlet port. In the following, for the convenience of description, positions of the lower substrate corresponding to the inlet port, the inlets and the outlet port in the upper substrate will be referred to as inlet port, inlets and outlet port of the lower substrate.

The raw material liquid drops (i.e., base materials for preparing the gene library) for extracting original DNA segments are provided to the first manipulation electrode array 401 from the inlet port 413, the first manipulation electrode array 401 comprising first inlets 414 (corresponding to the first inlets 114 in the upper substrate 102 of FIG. 2), and various reagents related to the preparation of the gene library are added via the first inlets 414, for example, DNA helicases, reagents for breaking DNA, DNA adapters or the like are added via four first inlets 114 respectively.

The corresponding manipulation electrodes are sequentially energized by means of the electrode control region, such that the raw material liquid drops move to the first inlets 414 along a path of the manipulation electrodes in the first manipulation electrode array 401. Now the original DNA segments added via the inlet port 413 and the reagents related to the preparation of the gene library added via the first inlets 414 can be mixed in the rectangular ring-shaped array 405 for preparing the gene library. The mixing process may comprise controlling an energizing sequence of the related manipulation electrodes to achieve circular flow of the raw material liquid drops and the related reagents, such that reactions involved in the preparation of the gene library is performed sufficiently.

Then, the prepared gene library enters via the manipulation electrodes 408 sequencing channels in the second manipulation electrode array 402, so as to perform sequencing. At this time, reagents for gene amplification are added via the second inlets 416 (corresponding to the position of the second inlets 116 in the upper substrate 102 of FIG. 2), and reagents for sequencing are added via the third inlets 417 (corresponding to the position of the third inlets 117 in the upper substrate 102 of FIG. 2), for example, four fluorescent labeled bases, so the prepared gene library is amplified while being sequenced in the second manipulation electrode array, and then flows out of the gene chip via the outlet port 419 (corresponding to the position of the outlet port 119 in the upper substrate 102 of FIG. 2) after the sequencing, thereby completing the gene sequencing.

Figure 5:
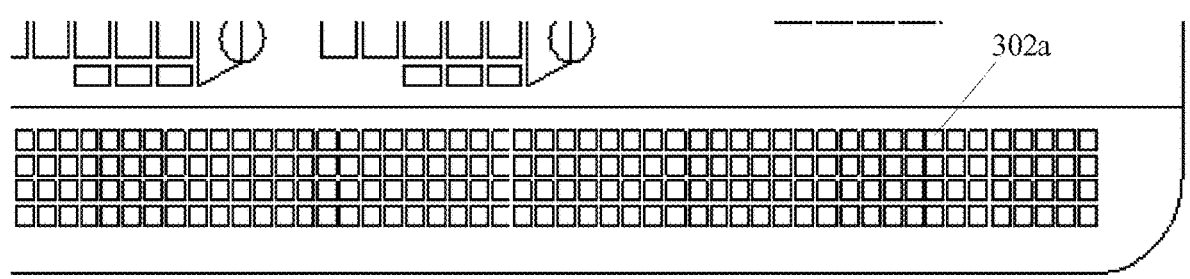
FIG. 5 is an enlarged schematic view of the electrode control region of the gene sequencing chip according to an embodiment of this disclosure.

Controlling the flow of the raw material liquid drops, the reagents related to gene library preparation, reagents related to gene amplification and reagents for sequencing within the first manipulation electrode array 401 and the second manipulation electrode array 402 is achieved by controlling an energizing sequence of the manipulation electrodes in the liquid drop operation region 301. The energization of the manipulation electrodes in the liquid drop operation region is controlled by means of the electrode control region 302 outside the liquid drop operation region 301. FIG. 5 is an enlarged schematic view of the electrode control region of the gene sequencing chip according to an embodiment of this disclosure. The manipulation electrodes in the liquid drop operation region 301 form an array, and the electrode control region 302 comprises a metal contact point array, metal contact points 302a in the metal contact point array being electrically connected with one or more manipulation electrodes in the liquid drop operation region 301, so different voltage signals can be applied to the manipulation electrodes via the metal contact point array.

Moreover, during the sequencing process, inlet amounts of different reagent liquid drops can be controlled accurately so that accurate metering control can be achieved during the entire sequencing process from library preparation to gene amplification and to sequencing.

Figure 6:
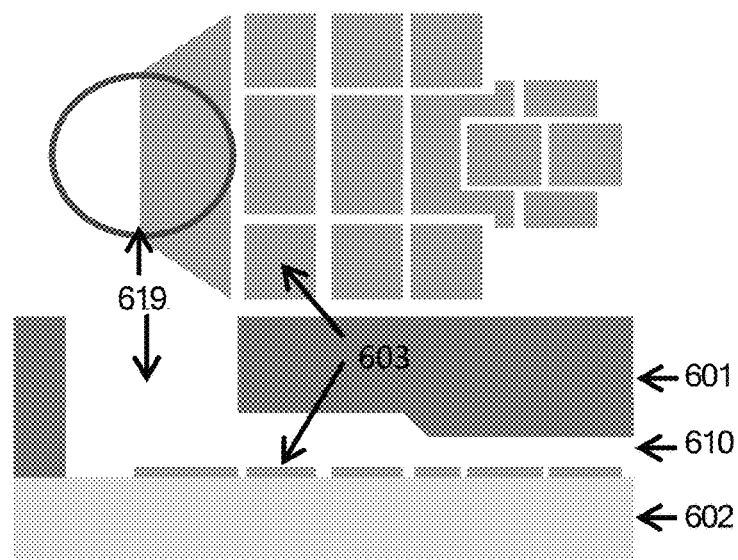
FIG. 6 is an enlarged schematic view of the inlet port/outlet port of the gene sequencing chip according to an embodiment of this disclosure.

FIG. 6 is an enlarged schematic view of the inlet port/outlet port of the gene sequencing chip according to an embodiment of this disclosure. As shown in FIG. 6, the upper substrate 601 is provided with an inlet port/outlet port 619, and manipulation electrodes 603 are arranged on the lower substrate 602. By applying a voltage to the manipulation electrodes 603 and taking advantage of the inlet port 619, large liquid drops can be split into small liquid drops, which enter a gap 610 between the upper and lower substrates and then arrive at the sub-arrays mentioned above. After the completion of the sequencing, small liquid drops in different sub-arrays can be fused into large liquid drops which are converged at the outlet port. Similar to the inlet port/outlet port 619, manipulation electrodes are provided at the inlets mentioned above, so as to control inlet amounts of different liquid drops, which will not be depicted herein for simplicity. The upper part of FIG. 6 schematically shows a plan view of the manipulation electrodes on the lower substrate 602, and the lower part of FIG. 6 shows a section view of the upper substrate 601, the lower substrate 602 and the manipulation electrodes.

With the gene sequencing chip according to the embodiments of this disclosure, operations to tiny liquid drops such as movement, fusion and splitting of the liquid drops can be accurately manipulated by using digital micro fluidic techniques, and all steps of the gene sequencing from library preparation to gene detection can be completed in a programmatic manner on one chip. The chip has a high degree of integration, the liquid drops can be manipulated accurately, the consumption of the reagents can be reduced, and the preparation process is simple and mature.

Other embodiments of this disclosure provide a gene sequencing method based on the gene sequencing chip according to any of the above embodiments, the method comprises the following steps: controlling the raw material liquid drops (i.e., base materials for preparing a gene library) for extracting original DNA segments to arrive at the first manipulation electrode array 401 of the liquid drop operation region 301 from the inlet port 413, controlling an energizing sequence for the manipulation electrodes, so as to enable the raw material liquid drops to flow along a path of the manipulation electrodes of the first sub-array 401.

Controlling reagent liquid drops related to gene library preparation to arrive at the first manipulation electrode array 401 from the first inlets 414, and then controlling the related reagent liquid drops to flow along channels of the first manipulation electrode array 401 and mix with the raw material liquid drops.

The raw material liquid drops and the reagents related to gene library preparation added via the first inlets 414 are mixed in the rectangular ring-shaped array 405, so as to prepare the gene library. The mixing process can comprise controlling an energizing sequence for the manipulation electrodes to achieve circular flow of the raw material liquid drops and the related reagent liquid drops, such that reactions involved in the preparation of the gene library is performed sufficiently.

Then, the prepared gene library is controlled to enter sequencing channels of the second manipulation electrode array 402 by controlling the energizing sequence for the manipulation electrodes, and the prepared gene library liquid drops flow along the second manipulation electrode array 402.

Reagent liquid drops related to gene amplification are added via the second inlets 416, and reagent liquid drops for sequencing are added via the third inlets 417, for example, four fluorescent labeled bases, so the prepared gene library is amplified while being sequenced in the second manipulation electrode array, and then flows out of the gene chip via the outlet port 419 after the sequencing, thereby completing the sequencing by the gene chip.

Controlling the flow of the raw material liquid drops, the reagent liquid drops related to gene library preparation, reagent liquid drops related to gene amplification and reagent liquid drops for sequencing within the first manipulation electrode array 401 and the second manipulation electrode array 402 is achieved by controlling an energizing sequence for the manipulation electrodes in the liquid drop operation region 301. The manipulation electrodes in the liquid drop operation region 301 are controlled by means of the electrode control region 302 arranged outside the liquid drop operation region 301. As shown in FIG. 6, the manipulation electrodes in the liquid drop operation region 301 are in an array, and the electrode control region 302 includes a metal contact point array, contact points of the metal contact point array are in one-to-one correspondence with the plurality of manipulation electrodes.

Controlling the liquid drops for test to arrive at the first manipulation electrode array of the liquid drop operation region from the inlet port comprises splitting the liquid drops for test from large liquid drops into small liquid drops which arrive at the first manipulation electrode array of the liquid drop operation region. Similar expressions such as "arrive at the first manipulation electrode array of the liquid drop operation region", "arrive at the second manipulation electrode array of the liquid drop operation region" and "arrive at the manipulation electrodes" mentioned in this disclosure do not mean that the liquid drops are in direct contact with the manipulation electrodes, but instead they indicate that the liquid drops are located in a position corresponding to the related manipulation electrodes, and the liquid drops may be located above the manipulation electrodes, but any other possible medium such as a hydrophobic layer may exist between the liquid drops and the manipulation electrodes. According to the gene sequencing method of this disclosure, operations to tiny liquid drops such as movement, fusion and splitting of the liquid drops can be accurately manipulated by using digital micro fluidic techniques, and all steps of the gene sequencing from library preparation to gene detection can be completed on one chip. The chip has a high degree of integration, the liquid drops can be manipulated accurately, the consumption of the reagents can be reduced, and the preparation process is simple and mature.

The movement, fusion or splitting of the liquid drops mentioned the embodiments of this disclosure are based on an electro wetting-on-dielectric (EWOD) principle, which will be explained briefly. Due to the existence of an upper hydrophobic layer and a lower hydrophobic layer, when the manipulation electrodes are not energized, the liquid drop has a contact angle of greater than 90 degrees with respect to a surface of the hydrophobic layer, and when a voltage is applied to the manipulation electrodes, the contact angle of the liquid drop will be changed. For example, for two adjacent manipulation electrodes, if the liquid drop is initially still on a left manipulation electrode, and now if a voltage is applied to the manipulation electrode on the right, the contact angle of the liquid drop will be changed (become smaller than 90 degrees), and the shape of the liquid drop will change, so that the liquid drop as a whole has a tendency of moving towards the manipulation electrode on the right. If the manipulation electrode on the right is continuously energized, the liquid drop will move towards the electrode on the right until it arrives at the manipulation electrode on the right. If voltage application to the manipulation electrode on the right stops, the liquid drop will stop at the manipulation electrode on the right.

Some embodiments of this disclosure and the technical principles applied therein are depicted above. Those skilled in the art should understand that the present invention is not limited to the embodiments herein, and for those skilled in the art, these embodiments can be obviously changed, adjusted and substituted without deviating from the protection scope of the invention. Therefore, more other equivalent embodiments can be obtained without deviating from the idea of the invention, and the scope of the invention is subject to the appended claims.

The invention claimed is:

1. A gene sequencing chip, comprising:
an upper substrate including a plurality of liquid inlets for inletting liquid drops,
a lower substrate opposite to the upper substrate and spaced therefrom by a gap for accommodating the liquid drops, the liquid drops comprising raw material liquid drops, gene library preparation reagent liquid drops, gene amplification reagent liquid drops and gene sequencing reagent liquid drops,
wherein the lower substrate comprises a liquid drop operation region, the liquid drop operation region comprises:
at least one first manipulation electrode array, each first manipulation electrode array comprising a plurality of first manipulation electrodes arranged in a row in a first direction and spaced apart from each other, the first manipulation electrode array being configured to move the raw material liquid drops and the gene library preparation reagent liquid drops;
at least one second manipulation electrode array, each second manipulation electrode array comprising a plurality of second manipulation electrodes arranged in a row in the first direction and spaced apart from each other, the second manipulation electrode array being configured to move the gene amplification reagent liquid drops and the gene sequencing reagent liquid drops; and
a rectangular ring-shaped array comprising a plurality of third manipulation electrodes spaced apart from each other and forming a rectangular shape, the rectangular ring-shaped array being configured to mix the raw material liquid drops and the gene library preparation reagent liquid drops,
wherein the second manipulation electrode array and the first manipulation electrode array are adjacent to each other in a second direction perpendicular to the first direction,
wherein the lower substrate further comprises an electrode control region for controlling an energizing sequence for the plurality of first manipulation electrodes, the plurality of second manipulation electrodes and the plurality of third manipulation electrodes to achieve movement of the liquid drops.

2. The gene sequencing chip according to claim 1, wherein the liquid drop operation region comprises a sample region, a first sample injection region, a second sample injection region and a third sample injection region, the sample region comprising a plurality of sample region manipulation electrodes adjoining the first manipulation electrode array, wherein the upper substrate further comprises:
an inlet port via which the raw material liquid drops are provided to the sample region;
a first inlet via which the gene library preparation reagent liquid drops are provided to the first sample injection region, the first sample injection region comprising a plurality of first sample injection region manipulation electrodes adjoining the first manipulation electrode array;
a second inlet via which the gene amplification reagent liquid drops are provided to the second sample injection region, the second sample injection region comprising a plurality of second sample injection region manipulation electrodes adjoining the second manipulation electrode array;
a third inlet via which the gene sequencing reagent liquid drops are provided to the third sample injection region, the third sample injection region comprising a plurality of third sample injection region manipulation electrodes adjoining the second manipulation electrode array, and
wherein the inlet port, the first inlet, the second inlet and the third inlet all penetrate the upper substrate.

3. The gene sequencing chip according to claim 1, wherein the upper substrate comprises an outlet port for discharging a waste liquid, and the outlet port penetrates the upper substrate.

4. The gene sequencing chip according to claim 1, wherein some first manipulation electrodes of the plurality of first manipulation electrodes of the first manipulation electrode array act as some third manipulation electrodes of the plurality of third manipulation electrodes of the rectangular ring-shaped array, so that the first manipulation electrode array comprises a side of the rectangular shape.

5. The gene sequencing chip according to claim 2, an area of an orthographic projection of the first sample injection region on the upper substrate is greater than an area of an orthographic projection of the third sample injection region on the upper substrate.

6. The gene sequencing chip according to claim 1, wherein the electrode control region comprises a metal contact point array, the metal contact point array comprises a plurality of metal contact points corresponding to the plurality of first manipulation electrodes, the plurality of second manipulation electrodes and a plurality of third manipulation electrodes.

7. The gene sequencing chip according to claim 1, wherein the lower substrate further comprises a first glass substrate for carrying the liquid drop operation region and the electrode control region.

8. The gene sequencing chip according to claim 1, wherein the lower substrate further comprises:
a first dielectric layer overlaying the liquid drop operation region, and
a first hydrophobic layer arranged on a surface of the first dielectric layer facing away from the first manipulation electrode array and the second manipulation electrode array.

9. The gene sequencing chip according to claim 1, the upper substrate comprises:
a second glass substrate,
an ITO reference electrode arranged on a surface of the second glass substrate facing the lower substrate,
a second dielectric layer arranged on a surface of the ITO reference electrode facing the lower substrate, and
a second hydrophobic layer arranged on a surface of the upper dielectric layer facing the lower substrate.

10. The gene sequencing chip according to claim 8, wherein the first hydrophobic layer comprises PTFE.

11. The gene sequencing chip according to claim 7, wherein an area of an orthographic projection of each first manipulation electrode of the first manipulation electrode array on the first glass substrate is greater than an orthographic projection of each second manipulation electrode of the second manipulation electrode array or each third manipulation electrode of the rectangular ring-shaped array on the first glass substrate.

12. The gene sequencing chip according to claim 1, wherein the gene sequencing chip comprises a plurality of first manipulation electrode arrays comprising the at least one first manipulation electrode array,
wherein respective one second manipulation electrode array of the at least one second manipulation electrode array is arranged between every two adjacent first manipulation electrode arrays of the plurality of first manipulation electrode arrays, respectively.

* * * * *